United States Patent [19]

Chibata et al.

[11] 4,224,411
[45] Sep. 23, 1980

[54] IMMOBILIZED AMINOACYLASE

[75] Inventors: Ichiro Chibata, Suita; Tetsuya Tosa, Kyoto; Takao Mori, Takatsuki; Taizo Watanabe, Nagaokakyo; Motoki Fujimura, Ikeda, all of Japan

[73] Assignee: Tanabe Seiyaku Co., Ltd., Osaka, Japan

[21] Appl. No.: 911,995

[22] Filed: Jun. 2, 1978

[30] Foreign Application Priority Data

Jul. 12, 1977 [JP] Japan .................................. 52/83680

[51] Int. Cl.$^3$ ...................... C12N 11/02; C12N 11/10; C12P 13/04
[52] U.S. Cl. .................................. 435/177; 435/106; 435/178
[58] Field of Search .................. 195/63, 68, DIG. 11, 195/29; 435/188, 180, 177, 178, 179, 174, 227, 106

[56] References Cited

U.S. PATENT DOCUMENTS

| 3,386,888 | 6/1968 | Chibata et al. | 195/63 X |
|---|---|---|---|
| 4,008,124 | 2/1977 | Fujita et al. | 195/68 X |
| 4,090,919 | 5/1978 | Chibeta et al. | 195/63 |

FOREIGN PATENT DOCUMENTS

1061717  3/1967  United Kingdom ..................... 435/227

OTHER PUBLICATIONS

Birnbaum, S. M., Aminoacylase, Methods In Enzymology, vol. II, Academic Press, Inc., New York, 1955, (pp. 115–119).

*Primary Examiner*—David M. Naff
*Attorney, Agent, or Firm*—Bierman & Bierman

[57] ABSTRACT

An immobilized aminoacylase preparation is obtained by adsorbing tannin on a water-insoluble, hydrophilic carrier to give a water-insoluble tannin preparation, adsorbing aminoacylase on the tannin preparation to give a water-insoluble tannin-aminoacylase preparation, and then binding ferric or ferrous ion thereto. The immobilized preparation obtained above sustains a high rate of enzymatic activity for a long period of time when used in an enzymatic reaction thereof with N-acyl-DL-amino acids.

2 Claims, No Drawings

IMMOBILIZED AMINOACYLASE

This invention relates to an immobilized aminoacylase preparation and a method for preparing the same. More particularly, it relates to a water-insoluble tanninaminoacylase preparation having ferric or ferrous ion bound thereto.

Aminoacylase has the ability to hydrolyze the L-isomer of a N-acyl-amino acid and can be used for the optical resolution of DL-amino acids. For example, L-amino acid is prepared by hydrolyzing a N-acyl-DL-amino acid asymmetrically with aminoacylase to give a mixture of the free L-amino acid and N-acyl-D-amino acid, and then separating said free acid from the N-acyl-D-amino acid by taking advantage of the difference in solubility thereof. However, this method is still unsatisfactory for large scale production of L-amino acids, because additional steps of removing the enzyme and other impurities from the reaction mixture are required to recover highly pure L-amino acids. Moreover, when the enzymatic reaction is completed, the reaction solution is boiled and/or acidified to destroy the enzyme, and the precipitates of the enzyme are filtered off. Thus, aminoacylase can be used only once and must be discarded thereafter.

Recently, immobilized aminoacylase has been employed to overcome the above-mentioned disadvantages. For example, U.S. Pat. No. 3,386,888 discloses the resolution of DL-amino acids by hydrolyzing N-acyl-derivatives thereof asymmetrically with an immobilized aminoacylase preparation. The aminoacylase preparation of said U.S. patent is prepared by adsorbing aminoacylase on an anion exchange resin such as diethylaminoethyl-dextran, diethylaminoethyl-cellulose or triethylaminoethyl-cellulose.

We have now found that a water-insoluble tanninaminoacylase preparation binding ferric or ferrous ion thereto can sustain a high rate of enzymatic activity for a long period of time when used in an enzymatic reaction thereof with N-acyl-DL-amino acid. We have also found that the above-mentioned preparation binds the aminoacylase firmly and does not liberate it from said preparation even in the presence of a high concentration of substrates.

An object of the present invention is to provide a novel immobilized aminoacylase preparation [i.e., an immobilized aminoacylase preparation comprising aminoacylase bound by adsorption to a water-insoluble tannin preparation (said tannin preparation consisting essentially of tannin bound by adsorption to a water-insoluble, hydrophilic carrier) and ferric or ferrous ion bound to said aminoacylase and/or said tannin preparation by ionic linkage]. Another object of the invention is to provide an immobilized aminoacylase preparation which sustains a high rate of enzymatic activity for a long period of time and which can be reused in a number of successive operations. A further object of the invention is to provide a stable immobilized aminoacylase preparation which does not liberate aminoacylase in the presence of a high concentration of substrates. A still further object of the invention is to provide a method for preparing the above-mentioned aminoacylase preparation. Other objects of the present invention will be apparent from the description which follows.

According to the present invention, the immobilized aminoacylase preparation can be prepared by the steps of:

(i) adsorbing tannin on a water-insoluble, hydrophilic carrier to give a water-insoluble tannin preparation, (ii) adsorbing aminoacylase on the water-insoluble tannin preparation to give a water-insoluble tanninaminoacylase preparation, and (iii) ionically binding ferric or ferrous ion thereto.

The term "hydrophilic" as used herein means that the carrier is made wettable or swellable in water but not substantially soluble therein.

Suitable examples of the carrier which are employed in the present invention include water-insoluble, hydrophilic polysaccharides having a group of the formula:

—A—R wherein R is hydrogen, amino, hydroxy, carboxyl or phenoxy, and A is alkylene having one to 16 carbon atoms which may be interrupted by a group selected from the class consisting of —O— and —NH—. Such polysaccharide derivatives include, for example, alkyl-polysaccharides such as alkyl-cellulose, alkyl-agarose or cross-linked alkyl-dextran (alkyl-dextran cross-linked with epichlorohydrin or divinylsulfone); aminoalkyl-polysaccharides such as aminoalkyl-cellulose, aminoalkyl-agarose or cross-linked aminoalkyl-dextran (aminoalkyl-dextran cross-linked with epichlorohydrin or divinylsulfone); hydroxyalkyl-polysaccharides such as hydroxyalkyl-cellulose, hydroxyalkyl-agarose or cross-linked hydroxyalkyl-dextran (hydroxyalkyl-dextran cross-linked with epichlorohydrin or divinylsulfone); carboxyalkyl-polysaccharides such as carboxyalkyl-cellulose, carboxyalkyl-agarose or cross-linked carboxyalkyl-dextran (carboxyalkyl-dextran cross-linked with epichlorohydrin or divinylsulfone); and phenoxyalkyl-polysaccharides such as phenoxyalkyl-cellulose, phenoxyalkyl-agarose or cross-linked phenoxyalkyl-dextran (phenoxyalkyl-cellulose cross-linked with epichlorohydrin or divinylsulfone).

The alkyl-polysaccharide may be prepared by activating a polysaccharide (e.g., cellulose, agarose or cross-linked dextran) with cyanogen halide (e.g., cyanogen chloride, cyanogen bromide), epihalohydrin (e.g., epichlorohydrin, epibromohydrin) or alkylene bisepoxide [e.g., $\alpha,\omega$-bis(2,3-epoxypropyl)alkane, $\alpha,\omega$-bis(2,3-epoxypropoxy)alkane] to give an activated polysaccharide, then reacting the activated polysaccharide with alkylamine (e.g., methylamine, ethylamine, propylamine, butylamine, hexylamine, octylamine, dodecylamine). Suitable examples of $\alpha,\omega$-bis(2,3-epoxypropyl)alkane and $\alpha,\omega$-bis(2,3-epoxypropoxy)alkane include $\alpha,\omega$-bis(2,3-epoxypropyl)ethane, $\alpha,\omega$-bis(2,3-epoxypropyl)butane, $\alpha,\omega$-bis(2,3-epoxypropoxy)ethane and $\alpha,\omega$-bis(2,3-epoxypropoxy)butane. Alternatively, the alkyl-polysaccharide may be prepared by reacting a polysaccharide with alkyl glycidyl ether (e.g., methyl, ethyl, butyl, pentyl, hexyl, octyl, decyl or dodecyl ether of 2,3-epoxypropanol).

The aminoalkyl-polysaccharide may be prepared by reacting the activated polysaccharide (i.e., those obtained above) with alkylenediamine (e.g., ethylenediamine, tetramethylenediamine, hexamethylenediamine, octamethylenediamine, decamethylenediamine, dodecamethylenedianime).

The hydroxyalkyl-polysaccharide may be prepared by reacting the activated polysaccharide with aminoalkanol [e.g., 2-aminoethanol, 3-amino-1-propanol, N-(aminoethyl)-ethanolamine, 2-(2-aminoethoxy)-ethanol]. Alternatively, the hydroxyalkyl-polysaccharide may be prepared by reacting the epihalohydrin- or alkylene bisepoxide-activated polysaccharide with alkylenediol (e.g., ethyleneglycol, tetramethyleneglycol, hexamethyleneglycol, octamethyleneglycol, decamethyleneglycol, dodecamethyleneglycol).

The carboxyalkyl-polysaccharide may be prepared by reacting the activated polysaccharide with aminoalkanoic acid (e.g., aminoacetic acid, aminopropionic acid, aminohexanoic acid, aminoheptanoic acid).

Further, the phenoxyalkyl-polysaccharide may be prepared by reacting a polysaccharide with phenyl glycidyl ether.

The above-mentioned reactions are shown by the following scheme. Throughout the scheme,

and (P)—OH stand for polysaccharide, X is halogen and A is the same as defined above. Further, B is a group of the formula; —(CH$_2$)$_n$— or —O(CH$_2$)$_n$O—, wherein n is an integer of one to 6.

(A) Activation of polysaccharide (Reaction 1)

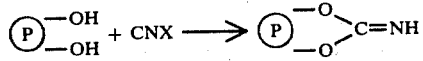

(cyanogen halide)　(cyanogen halide-activated polysaccharide)

(Reaction 2)

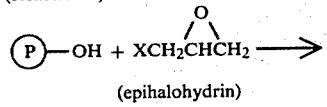
(epihalohydrin)

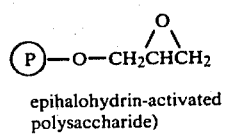
epihalohydrin-activated polysaccharide)

(Reaction 3)

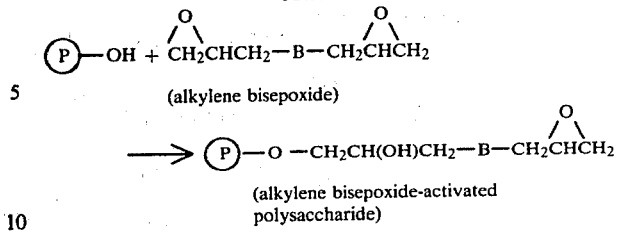
(alkylene bisepoxide)

(alkylene bisepoxide-activated polysaccharide)

(B) Synthesis of the alkyl-polysaccharide (Reaction 4)

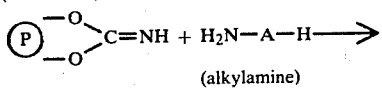
(alkylamine)

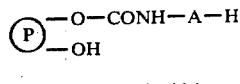
(alkyl-polysaccharide)

(Reaction 5)

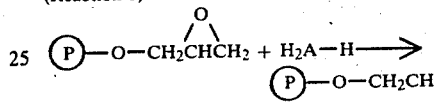

(alkyl-polysaccharide)

(Reaction 6)

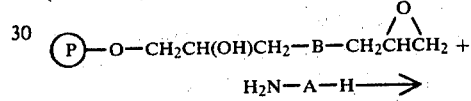

(alkyl-polysaccharide)

(Reaction 7)

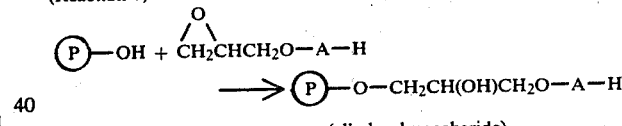
(alkyl-polysaccharide)

(C) Synthesis of the aminoalkyl-polysaccharide (Reaction 8)

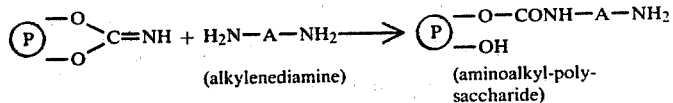
(alkylenediamine)　(aminoalkyl-polysaccharide)

(Reaction 9)

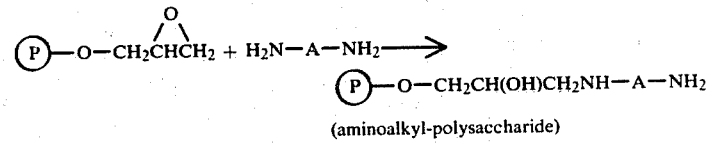
(aminoalkyl-polysaccharide)

(Reaction 10)

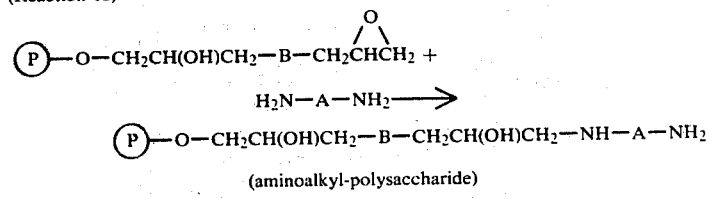
(aminoalkyl-polysaccharide)

(D) Synthesis of the hydroxyalkyl-polysaccharide (Reaction 11)

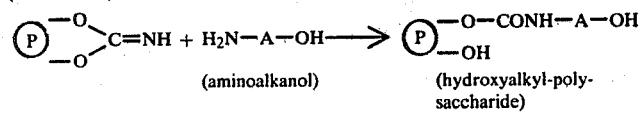
(aminoalkanol) (hydroxyalkyl-polysaccharide)

(Reaction 12)

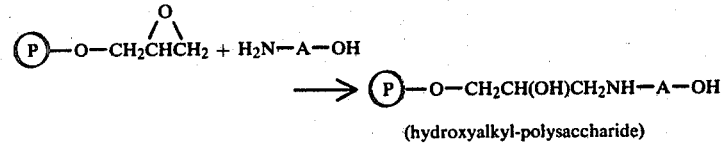
(hydroxyalkyl-polysaccharide)

(Reaction 13)

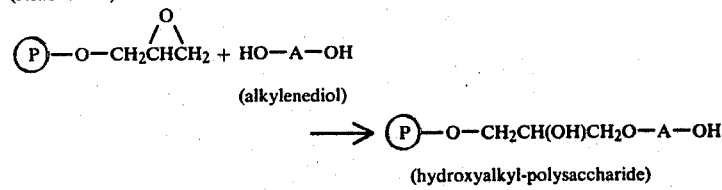
(alkylenediol)
(hydroxyalkyl-polysaccharide)

(Reaction 14)

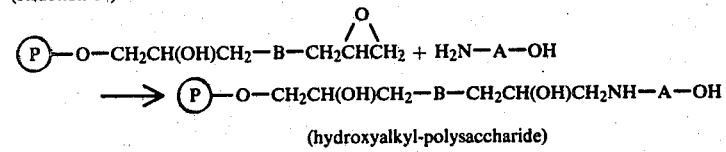
(hydroxyalkyl-polysaccharide)

(Reaction 15)

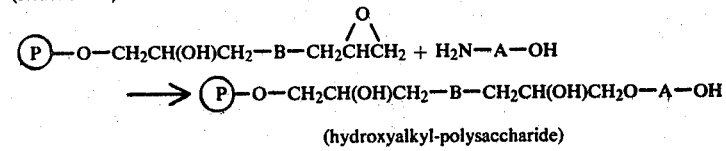
(hydroxyalkyl-polysaccharide)

(E) Synthesis of the carboxyalkyl-polysaccharide (F) Synthesis of the phenoxyalkyl-polysaccharide

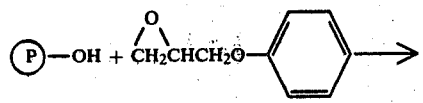
(Reaction 19)

(Reaction 16)

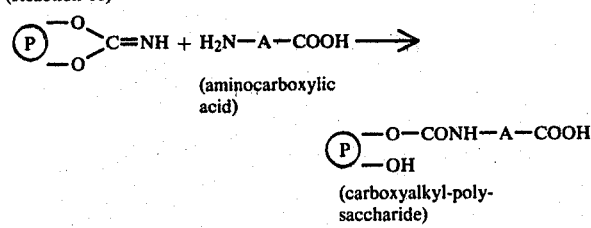
(aminocarboxylic acid)
(carboxyalkyl-polysaccharide)

(Reaction 17)

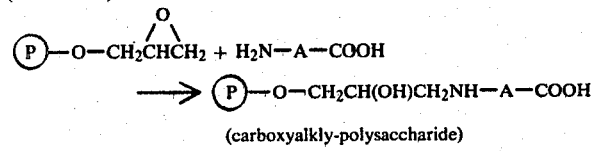
(carboxyalkly-polysaccharide)

(Reaction 18)

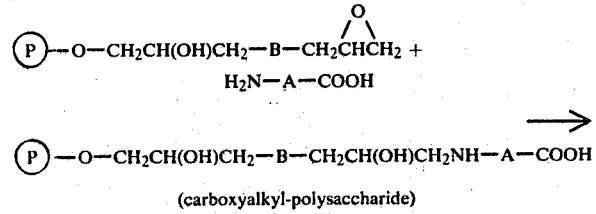
(carboxyalkyl-polysaccharide)

-continued

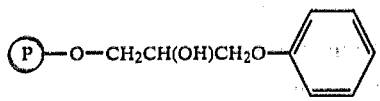

(phenoxyalkyl-polysaccharide)

When illustrating these reactions by taking into account the reaction formulae shown herein, the activation of the polysaccharide with cyanogen halide (Reaction 1) may be carried out at 4° to 40° C. at a pH of 8 to 12 in an aqueous solvent (e.g., water). On the other hand, the activation of the polysaccharide with epihalohydrin or alkylene bisepoxide (Reactions 2 and 3) may be carried out at 30° to 100° C. at a pH of 9 to 14 in an aqueous solvent (e.g., water). When cellulose is employed as the polysaccharide, it is preferred to treat said cellulose with an aqueous sodium hydroxide solution prior to the activation reaction.

The subsequent reactions of the cyanogen halide-activated polysaccharide with alkylamine, alkylenediamine, aminoalkanol or aminoalkanoic acid (Reactions 4,8,11 and 16) may be carried out at 4° to 40° C. at a pH of 8 to 12 in an aqueous solvent (e.g./. water). On the other hand, the reactions of the epihalohydrin- or alkylene bisepoxide- activated polysaccharide with alkylamine, alkylenediamine, alkylenediol or aminoalkylcarboxylic acid (Reactions 5,6,9,10,12,13, 14, 15, 17 and 18) may be carried out at 30° to 100° C. at a pH of 9 to 14 in an aqueous solvent (e.g., water).

The reactions of polysaccharide with alkyl glycidyl ether or phenyl glycidyl ether (Reactions 7 and 19) may be carried out at 30° to 100° C. in an aqueous solvent (e.g., water, aqueous methanol, aqueous ethanol).

The alkyl-, aminoalkyl-, hydroxyalkyl-, carboxylkyl- or phenoxyalkyl-polysaccharides of the present invention are not limited to those which are prepared specifically by the above-mentioned methods, but any polysaccharides which have a group of the formula: —A—R (R and A are the same as defined above) may be employed for the purpose of the present invention.

Examples of the alkyl-, aminoalkyl-, hydroxyalkyl-, carboxyalkyl- or phenoxyalkyl-polysaccharides of the present invention include cellulose—O—CONH(CH$_2$)H, cellulose—O—CONH(CH$_2$)$_2$H, cellulose—O—CONH(CH$_2$)$_6$H, agarose—O—CONH(CH$_2$)$_2$H, agarose—O—CONH(CH$_2$)$_6$H, a cross-linked dextran—O—CONH(CH$_2$)$_6$H, cellulose—O—CH$_2$CH(OH)CH$_2$NH(CH$_2$)$_2$H, cellulose—O—CH$_2$CH(OH)CH$_2$NH(CH$_2$)$_3$H, cellulose—O—CH$_2$CH(OH)CH$_2$NH(CH$_2$)$_8$H, agarose—O—CH$_2$CH(OH)CH$_2$NH(CH$_2$)$_3$H, agarose—O—CH$_2$CH(OH)CH$_2$NH—(CH$_2$)$_8$H, a cross-linked dextran—O—CH$_2$CH(OH)CH$_2$NH(CH$_2$)$_3$H, a cross-linked dextran—O—CH$_2$CH(OH)CH$_2$NH(CH$_2$)$_8$H, cellulose—O—CH$_2$CH(OH)CH$_2$O(CH$_2$)$_2$NH(CH$_2$)$_2$H, agarose—O—CH$_2$CH(OH)CH$_2$O(CH$_2$)$_2$—NH(CH$_2$)$_4$H, cellulose—O—CH$_2$CH(OH)CH$_2$O(CH$_2$)$_4$OCH$_2$CH(OH)CH$_2$—NH(CH$_2$)$_2$H, cellulose—O—CH$_2$CH(OH)CH$_2$O(CH$_2$)$_4$OCH$_2$CH(OH)CH$_2$—NH(CH$_2$)$_3$H, cellulose—O—CONH(CH$_2$)$_2$NH$_2$, cellulose—O—CONH—(CH$_2$)$_6$NH$_2$, cellulose—O—CONH(CH$_2$)$_{10}$NH$_2$, agarose—O—CONH—(CH$_2$)$_6$NH$_2$, agarose—O—CONH(CH$_2$)$_8$NH$_2$, a cross-linked dextran—O—CONH(CH$_2$)$_6$NH$_2$, cellulose—O—CH$_2$CH(OH)CH$_2$NH(CH$_2$)$_4$NH$_2$, cellulose—O—CH$_2$CH(OH)CH$_2$NH(CH$_2$)$_6$NH$_2$, cellulose—O—CH$_2$CH(OH)—CH$_2$NH(CH$_2$)$_8$NH$_2$, cellulose—O—CH$_2$CH(OH)CH$_2$NH(CH$_2$)$_{10}$NH$_2$, cellulose—O—CH$_2$CH$_2$CH(OH)CH$_2$NH(CH$_2$)$_{12}$NH$_2$, agarose—O—CH$_2$—CH(OH)CH$_2$NH(CH$_2$)$_4$NH$_2$, agarose—O—CH$_2$CH(OH)CH$_2$NH(CH$_2$)$_6$NH$_2$, agarose—O—CH$_2$CH(OH)CH$_2$NH(CH$_2$)$_8$NH$_2$, a cross-linked dextran—O—CH$_2$CH(OH)CH$_2$NH(CH$_2$)$_4$NH$_2$, a cross-linked dextran—O—CH$_2$—CH(OH)CH$_2$NH(CH$_2$)$_6$NH$_2$, a cross-linked dextran—O—CH$_2$CH(OH)—CH$_2$NH(CH$_2$)$_8$NH$_2$, cellulose—O—CONH(CH$_2$)$_2$OH, cellulose—O—CONH(CH$_2$)$_3$OH, cellulose—O—CONH(CH$_2$)$_2$O(CH$_2$)$_2$OH, agarose—O—CONH(CH$_2$)$_3$OH, cellulose—O—CH$_2$CH(OH)CH$_2$NH(CH$_2$)$_2$OH, cellulose—O—CH$_2$CH(OH)CH$_2$NH(CH$_2$)$_4$OH, cellulose—O—CH$_2$CH(OH)CH$_2$—NH(CH$_2$)$_2$O(CH$_2$)$_2$OH, cellulose—O—CH$_2$CH(OH)CH$_2$O(CH$_2$)$_6$OH, cellulose—O—CH$_2$CH(OH)CH$_2$O(CH$_2$)$_4$OCH$_2$CH(OH)CH$_2$NH(CH$_2$)$_4$OH, cellulose—O—CONH(CH$_2$)$_3$COOH, cellulose—O—CONH(CH$_2$)$_5$COOH, agarose—O—CONH(CH$_2$)$_3$COOH, agarose—O—CONH(CH$_2$)$_5$COOH, a cross-linked dextran—O—CONH(CH$_2$)$_5$COOH, cellulose—O—CH$_2$CH(OH)—CH$_2$NH(CH$_2$)$_3$COOH, cellulose—O—CH$_2$CH(OH)CH$_2$NH(CH$_2$)$_3$COOH, cellulose—O—CH$_2$CH(OH)CH$_2$NH(CH$_2$)$_5$COOH, agarose—O—CH$_2$CH(OH)—CH$_2$NH(CH$_2$)$_3$COOH, agarose—O—CH$_2$CH(OH)CH$_2$NH(CH$_2$)$_5$COOH, a cross-linked dextran—O—CH$_2$CH(OH)CH$_2$(CH$_2$)$_5$COOH, cellulose—O—CH$_2$CH(OH)CH$_2$O(CH$_2$)$_4$OCH$_2$CH(OH)CH$_2$NH(CH$_2$)$_5$COOH,

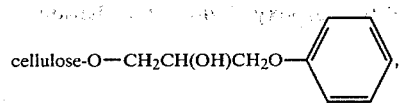

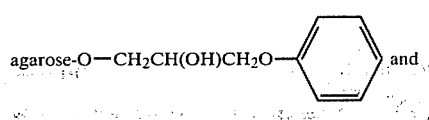

"Tannin" is the general term for astringent, aromatic acidic glucosides or polyphenols found in various plants and trees and, depending on the structures thereof, can be divided into two groups: (a) pyrogallol tannin (i.e., mono-, di- and/or trigalloyl monosaccharide, mono-, di- and/or trigalloyl disaccharides, and mono-, di- and-/or trigalloyl trisaccharides); and (b) catechol tannin (i.e., polyhydroxyphenol condensates and polyhydroxyflavon condensates). Examples of pyrogallol tannin include gallotannin, pentagalloyl glucose, Hamameli tannin and Acetannin. Examples of catechol tannin are polycatechol, polyepicatechol, polycatechin, poly(pistacia catechol) and poly(galloyl epicatechol). All of these pyrogallol and catechol tannins can be employed in the present invention. For making the water-insoluble tannin preparation, however, these tannins need not necessarily be in pure form, but crude products obtained from plants and trees may be employed without purification. For example, crude pyrogallol tannins such as chinese gallotannin or nutgallstannin and crude catechol tannin such as persimmon tannin are preferably used for the purpose of the present invention.

(The water-insoluble tannin preparation)

The water-insoluble tannin preparation can be prepared by adsorbing tannin on the water-insoluble hydrophilic carrier. The adsorption procedure may be readily performed by contacting said carrier with said tannin in an aqueous solvent (e.g., water). For example, the adsorption procedure is carried out by suspending the carrier in an aqueous tannin solution and then stirring or shaking the suspension. A suitable concentration of tannin in the solution may be between about 0.5 and 10 w/v%. It is preferred to carry out the adsorption at a temperature of 0° to 50° and at a pH of 3 to 10. After the above-mentioned operation, the water-insoluble tannin preparation (i.e., tannin bound by adsorption to the carrier) can be readily recovered by filtering or centrifuging the suspension to collect the precipitates, followed by washing the precipitates with water.

The water-insoluble tannin preparation obtained above, if required, may be treated with an oxidizing agent (e.g., potassium persulfate). For example, said tannin preparation is suspended in an aqueous potassium persulfate solution, and the suspension is allowed to stand at a temperature of 10° to 30° C. By this operation, the tannin adsorbed on the carrier is partially oxidized to give a partially oxidized water-insoluble tannin preparation. The partially oxidized water-insoluble tannin preparation can be recovered by filtering or centrifuging the suspension to collect the precipitates. When the partially oxidized water-insoluble tannin preparation thus obtained is employed as the tannin preparation in the subsequent steps, it can give an immobilized aminoacylase preparation of higher activity than the tannin preparation which is not treated with the oxidizing agent.

(The water-insoluble tannin-aminoacylase preparation)

The water-insoluble tannin-aminoacylase preparation can be prepared by adsorbing aminoacylase on the water-insoluble tannin preparation. The adsorption procedure may be readily performed by contacting aminoacylase with the water-insoluble tannin preparation in an aqueous solvent (e.g., water). For example, the water-insoluble tannin preparation is suspended in an aqueous aminoacylase solution, and the suspension is stirred. Aminoacylase need not necessarily be in pure form but crude aminoacylase solutions may be employed in the adsorption step.

For example, extracts of animal tissues and cellfree extracts of microorganisms may be preferable used as the aminoacylase solution. It is preferred to carry out the adsorption at a temperature of 0° to 40° C. and at a pH of 6.5 to 10. It is also preferred to carry out the adsorption at an ionic strength of 0 to 1.0. The aminoacylase activity of the water-insoluble tannin-aminoacylase preparation may be increased by carrying out the adsorption step in the presence of an organic solvent such as lower alkanols (e.g., n-butanol), ethyleneglycol or acetone.

By the above-mentioned operation, aminoacylase is adsorbed on the tannin preparation to form a water-insoluble tannin-aminoacylase preparation. After the above-mentioned operation the water-insoluble tannin-aminoacylase preparation (i.e., aminoacylase bound by adsorption to the tannin preparation) can be readily recovered by filtering or centrifuging the suspension to collect the precipitates followed by washing the precipitates with water.

Alternatively, the adsorption of aminoacylase on the water-insoluble tannin preparation may be conducted by a column method. For example, the water-insoluble tannin preparation is charged into a column. By passing an aqueous aminoacylase solution through the column at a suitable flow rate, the aminoacylase is adsorbed on the column of the tannin preparation. After this operation, the water-insoluble tannin-aminoacylase preparation is obtained by washing the column with water.

(The water-insoluble tannin-aminoacylase preparation binding ferric or ferrous ion thereto)

The water-insoluble tannin-aminoacylase preparation binding ferric or ferrous ion thereto can be prepared by ionically binding ferric or ferrous ion to the water-insoluble tannin-aminoacylase preparation. The ionic binding is carried out by contacting the water-insoluble tannin-aminoacylase preparation with ferric or ferrous ion in an aqueous solvent (e.g., water). For example, the tannin-aminoacylase preparation is suspended in an aqueous solvent (e.g., water), and an aqueous solution containing ferric or ferrous ion is added to the suspension. An aqueous solution of an inorganic ferric or ferrous salt (e.g., ferric chloride, ferric nitrate, ferrous chloride, ferrous sulfate) or an aqueous solution of an organic ferric or ferrous salt (e.g., ferric tartrate, terric citrate, ferrous fumarate, ferrous succinate) is suitable as the aqueous solution containing ferric or ferrous ion. It is preferred to carry out the operation at a temperature of 0° to 25° C. and at a pH of 6.5 to 7.5. By the above-mentioned operation, ferric or ferrous ion is bound ionically to the tannin-aminoacylase preparation. Further, the enzymatic activity of the tannin-aminoacylase preparation binding ferric or ferrous ion thereto can be increased by carrying out said operation (i.e., the ionic binding) in the presence of a N-acetyl-DL-amino acid (e.g., N-acetyl-DL-methionine). After the above-mentioned operation, the water-insoluble tannin-aminoacylase preparation binding ferric or ferrous ion thereto can be readily recovered by filtering or centrifuging the suspension to collect the precipitates, followed by washing the precipitates with water.

The immobilized aminoacylase preparation obtained by the above-mentioned method, i.e., the water-insoluble tannin-aminoacylase preparation binding ferric or ferrous ion thereto, retains a high level of enzymatic activity for a long period of time and is used as a heterogeneous catalyst to induce asymmetrical hydrolysis of a N-acyl-DL-amino acid. Moreover, since the binding among aminoacylase, tannin and the carrier is strengthened by means of ferric or ferrous ion, the immobilized aminoacylase preparation of the present invention can be used repeatedly in an enzymatic reaction with substrates. This is due to the absence of a substantial amount of desorption of the bound aminoacylase during the enzymatic reaction even with the addition of a high concentration of substrates.

Practical and presently preferred embodiments of the present invention are shown in the following Examples.

EXAMPLE 1

(1) 4 g of cellulose powder (manufactured by Toyo Roshi Co. under the trade name "Cellulose Powder D") are added to 60 ml of an aqueous 12% sodium hydroxide solution, and the mixture is allowed to stand at 5° to 10° C. for 30 minutes. The wet cellulose is collected by filtration and washed with water. 10 g of the wet cellulose thus obtained are suspended in 100 ml of an aqueous 1 N sodium hydroxide solution, and 10 ml of epichlorohydrin are added thereto. The suspension is stirred vigorously at 60° C. for 30 minutes. After the reaction is completed, the precipitates are collected by filtration and washed with water. The epichlorohydrin-activated cellulose thus obtained is suspended in 80 ml of an aqueous solution (adjusted to pH 10) of hexamethylenediamine (hexamethylenediamine content: 2.2 g/80 ml). The suspension is stirred slowly at 60° C. for 2 hours. After the reaction is completed, the precipitates are collected by filtration and washed successively with an aqueous 0.1 M sodium bicarbonate solution and water. 20 g (wet form) of an aminohexylcellulose [i.e., cellulose—O—$CH_2CH(OH)CH_2NH(CH_2)_6NH_2$] are thereby obtained.

(2) 400 ml of an aqueous 1% chinese gallotannin solution (adjusted to pH 7.0) are added to 20 g (wet form) of the aminohexyl-cellulose obtained in paragraph (1). The mixture is stirred at 25° C. for 2 hours. Then, the precipitates are collected by filtration and washed with water. 32 g (wet form) of a water-insoluble tannin preparation [i.e., chinese gallotannin bound by adsorption to the aminohexyl-cellulose] are thereby obtained.

(3) 800 mg of aminoacylase (30μ moles/hr/mg) are dissolved in 24 ml of an aqueous 0.2 M sodium chloride solution (pH 8.0) containing 2% of butanol. The aminoacylase solution thus obtained is added to 2 g (wet form) of the water-insoluble tannin preparation obtained in paragraph (2). The mixture is stirred at 37° C. for 60 minutes. Then, the precipitates are collected by filtration and washed with water. 2 g (wet form) of a water-insoluble tannin-aminoacylase preparation [i.e., aminoacylase bound by adsorption to the water-insoluble tannin preparation] are thereby obtained.

(4) 2 g (wet form) of the water-insoluble tannin-aminoacylase preparation obtained in paragraph (3) are suspended in 50 ml of water. 10 ml of an aqueous 2% ferric chloride solution are added gradually to the suspension while keeping the suspension at a pH of about 7.0 with sodium hydroxide. The precipitates are collected by filtration and washed with water. 2 g (wet form) of an immobilized aminoacylase preparation [i.e., water-insoluble tannin-aminoacylase preparation binding ferric ion thereto] are thereby obtained. The immobilized aminoacylase preparation thus obtained shows an aminoacylase activity of 4,140μ moles/hr/2 g (wet form) of said preparation. [The aminoacylase activity is determined by reacting the immobilized aminoacylase preparation with an aqueous 0.2 M N-acetyl-DL-methionine solution at 37° C. at a pH of 7.0. Said activity is estimated in terms of μ mole of L-methionine produced in one hour.]

(5) 5 ml of the immobilized aminoacylase preparation [i.e., the water-insoluble tannin-aminoacylase preparation binding ferric ion thereto] obtained in paragraph (4) are charged in a column. An aqueous 0.6 M N-acetyl-DL-methionine solution (pH 7.0) containing $5 \times 10^{-4}$ M of cobaltous ion is passed through the column at 30° C. at a flow rate of 6 ml/hr. The effluent is collected at intervals by passing the above-mentioned solution at a flow rate of 36 ml/hr. The aminoacylase activity of the immobilized aminoacylase praparation is estimated by assaying the amount of L-methionine in the effluent.

Just for comparison, 5 ml of the water-insoluble tannin-aminoacylase preparation obtained in paragraph (3) are treated in the same manner as above. The results are shown in Table 1.

Table I

| Operation time (days) | Aminoacylase activity (μ moles/ml) | | | |
|---|---|---|---|---|
| | The water-insoluble tannin-amninoacylase preparation binding ferric ion thereto | | The water-insoluble tannin-aminoacylase preparation | |
| 0 | 128 | (100) | 81 | (100) |
| 1 | 142 | (111) | 69 | (85) |
| 3 | 128 | (100) | 65 | (80) |
| 7 | 121 | (95) | 58 | (72) |
| 10 | 108 | (84) | 51 | (63) |

Note:
Numerical values shown in parentheses stand for the potency ratio of the aminoacylase activity calculated by the following formula:

$$\left[ \frac{\text{Aminoacylase activity estimated after a period of time especified in Table 1}}{\text{Initial aminoacylase activity}} \right] \times 100$$

EXAMPLE 2

(1) 2 g (wet form) of the water-insoluble tannin-aminoacylase preparation obtained in the same manner as described in Example 1-(3) are suspended in 25 ml of an aqueous 0.2 M N-acetyl-DL-methionine solution (pH 7.0) containing $5 \times 10^{-4}$ M of cobaltous ion. 2 ml of an aqueous 5% ferric chloride solution are added slowly to the suspension while keeping the suspension at a pH of about 7.0 with sodium hydroxide. Then, the precipitates are collected by filtration and washed with water. 2 g (wet form) of an immobilized aminoacylase preparation [i.e., water-insoluble tannin-aminoacylase preparation binding ferric ion thereto] are thereby obtained. The immobilized aminoacylase preparation thus obtained shows an aminoacylase activity of 4,600μ moles/hr/2 g (wet form) of said preparation.

(2) 5 ml of the immobilized aminoacylase preparation [i.e., the water-insoluble tannin-aminoacylase preparation binding ferric ion thereto] obtained in paragraph (1) are charged into a column. An aqueous N-acetyl-DL-amino acid solution shown in Table 2 is passed through the column at a space velocity (SV) specified therein. The aminoacylase activity of the immobilized aminoacylase preparation is estimated by assaying the amount of L-amino acid produced in the effluent. The results are shown in Table 2.

Table 2

| | Aminoacylase activity (μ moles/ml) | | | |
|---|---|---|---|---|
| Operation time (days) | 0.6 M acetyl-DL-methionine solution (SV = 1.4) | 0.5 M acetyl-DL-valine solution (SV = 1.42) | 0.4 M acetyl-DL-phenyl-alanine solution (SV = 1.5) | 0.2 M acetyl-DL-tryptophan solution (SV = 2) |
| 0 | 285 | 250 | 198 | 99 |
| 10 | 294 | 245 | 200 | 103 |
| 20 | 270 | 248 | 200 | 98 |
| 30 | 264 | 250 | 195 | 95 |
| 40 | 244 | 255 | 190 | 97 |
| 50 | 250 | 250 | 195 | 92 |
| 60 | 217 | 250 | 195 | 96 |

EXAMPLE 3

(1) 20 g (wet form) of a n-octyl-cellulose [i.e., cellulose—O—CH$_2$CH(OH)CH$_2$NH(CH$_2$)$_8$H] are prepared in the same manner as described in Example 1-(1) except that 3 g of n-octylamine are used instead of 2.2 g of hexamethylenediamine. 20 g (wet form) of the n-octyl-cellulose thus obtained are treated in the same manner as described in Example 1-(2), whereby 32 g (wet form) of a water-insoluble tannin preparation [i.e., chinese gallotannin bound by adsorption to the n-octyl-cellulose] are obtained.

(2) 2 g (wet form) of the water-insoluble tannin preparation obtained in paragraph (1) are treated in the same manner as described in paragraphs (3) and (4) of Example 1, whereby 2 g (wet form) of an immobilized aminoacylase preparation [i.e., water-insoluble tannin-aminoacylase preparation binding ferric ion thereto] are obtained. The immobilized aminoacylase preparation thus obtained shows an aminoacylase activity of 3,450μ moles/hr/2 g (wet form) of said preparation.

EXAMPLE 4

(1) 20 g (wet form) of a carboxypentyl-cellulose [i.e., cellulose—O—CH$_2$CH(OH)CH$_2$NH(CH$_2$)$_5$COOH] are prepared in the same manner as described in Example 1-(1) except that 2.5 g of ε-aminocaproic acid are used instead of 2.2 g of hexamethylenediamine. 20 g (wet form) of the carboxypentyl-cellulose thus obtained are treated in the same manner as described in Example 1-(2), whereby 32 g (wet form) of a water-insoluble tannin preparation [i.e., chinese gallotannin bound by adsorption to the carboxypentylcellulose] are obtained.

(2) 2 g (wet form) of the water-insoluble tannin preparation obtained in paragraph (1) are treated in the same manner as described in paragraphs (3) and (4) of Example 1, whereby 2 g (wet form) of an immobilized aminoacylase preparation [i.e., water-insoluble tannin-aminoacylase preparation binding ferric ion thereto] are obtained. The immobilized aminoacylase preparation thus obtained shows an aminoacylase activity of 3,584μ moles/hr/2 g of said preparation.

EXAMPLE 5

(1) 20 g (wet form) of a hydroxyalkyl-cellulose [i.e., cellulose—O—CH$_2$CH(OH)CH$_2$NH(CH$_2$)$_2$O(CH$_2$)$_2$OH] are obtained in the same manner as described in Example 1-(1) except that 2.5 ml of diglycolamine (i.e., 2-(2-aminoethoxy) ethanol) are used instead of 2.2 g of hexamethylenediamine. 20 g (wet form) of the hydroxyalkyl-cellulose thus obtained are treated in the same manner as described in Example 1-(2), whereby 32 g (wet form) of a water-insoluble tannin preparation [i.e., chinese gallotannin bound by adsorption to the hydroxyalkyl-cellulose] are obtained.

(2) 2 g (wet form) of the water-insoluble tannin preparation obtained in paragraph (1) are treated in the same manner as described in paragraphs (3) and (4) of Example 1, whereby 2 g (wet form) of an immobilized aminoacylase preparation [i.e., water-insoluble tannin-aminoacylase preparation binding ferric ion thereto] are obtained. The immobilized aminoacylase preparation thus obtained shows an aminoacylase activity of 3,345μ moles/hr/2 g (wet form) of said preparation.

EXAMPLE 6

(1) 4 g of cellulose powder (manufactured by Toyo Roshi Co. under the trade name "Cellulose Powder D") are added to 30 ml of an aqueous 25% sodium hydroxide solution, and the mixture is allowed to stand at 10° C. for 30 minutes. The wet cellulose is collected by filtration. One ml of phenyl glycidyl ether is dissolved in 70 ml of 50% ethanol, and the solution is added to the wet cellulose obtained above. The mixture is shaken at 60° C. for 2 hours. After the reaction is completed, the precipitates are collected by filtration and washed with 50% ethanol. 20 g (wet form) of a phenoxyalkyl-cellulose

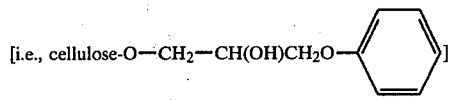

are thereby obtained.

(2) 20 g (wet form) of the phenoxyalkyl-cellulose obtained in paragraph (1) are treated in the same manner as described in Example 1-(2), whereby 32 g (wet form) of water-insoluble tannin preparation [i.e., chinese gallotannin bound by adsorption to the phenoxyalkyl-cellulose] are obtained.

(3) 2 g (wet form) of the water-insoluble tannin preparation obtained in paragraph (2) are treated in the same manner as described in paragraphs (3) and (4) of Example 1, whereby 2 g (wet form) of an immobilized aminoacylase preparation [i.e., water-insoluble tannin-aminoacylase preparation binding ferric ion thereto] are obtained. The immobilized aminoacylase preparation thus obtained shows an aminoacylase activity of 3,169μ moles/hr/2 g (wet form) of said preparation.

EXAMPLE 7

(1) 4 g of cellulose powder (manufactured by Toyo Roshi Co. under the trade name "Cellulose Powder D") are added to 60 ml of an aqueous 16% sodium hydroxide solution. The mixture is allowed to stand at 10° C. for 30 minutes, and 10 ml of epichlorohydrin are added thereto. The resultant mixture is stirred vigorously at 40° C. for 30 minutes. After the reaction is completed, the precipitates are collected by filtration and washed with water. The epichlorohydrin-activated cellulose thus obtained is treated in the same manner as described in Example 1-(1), whereby 20 g (wet form) of an aminohexyl-cellulose [i.e., cellulose-O—CH$_2$CH(OH)CH$_2$NH(CH$_2$)$_6$NH$_2$] are obtained.

(2) 50 ml of an aqueous 5% chinese gallotannin solution (adjusted to a pH of 7.0) are added to 20 g (wet form) of the aminohexyl-cellulose obtained in paragraph (1). The mixture is shaken at 25° C. for 2 hours. Then, the precipitates are collected by filtration and washed with water. 32 g (wet form) of a water-insoluble tannin preparation [i.e., chinese gallotannin bound by adsorption to the aminohexyl-cellulose] are thereby obtained.

(3) 2 g (wet form) of the water-insoluble tannin preparation obtained in paragraph (2) are treated in the same manner as described in paragraphs (3) and (4) of Example 1, whereby 2 g (wet form) of an immobilized aminoacylase preparation [i.e., water-insoluble tannin-aminoacylase preparation binding ferric ion thereto] are obtained. The immobilized aminoacylase preparation thus obtained shows an aminoacylase activity of 4,000μ moles/hr/2 g (wet form) of said preparation.

EXAMPLE 8

(1) 50 ml of an aqueous 1 N sodium hydroxide solution and 10 ml of epichlorohydrin are added to 10 g (wet form) of a cross-linked dextran (manufactured by Pharmacia Fine Chemicals under the trade name "Sephadex G-25"). The mixture is shaken at 60° C. for 30 minutes. After the reaction is completed, the precipitates are collected by filtration and washed with water. The epichlorohydrin-activated cross-linked dextran thus obtained is suspended in 50 ml of an aqueous solution (adjusted to a pH of 11) of hexamethylenediamine (hexamethylenediamine content: 0.5 g/50 ml), and the mixture is stirred slowly at 60° C. for 2 hours. After the reaction is completed, the precipitates are collected by filtration and washed with water. 16 g (wet form) of a cross-linked aminohexyl-dextran [i.e., a cross-linked dextran—O—$CH_2CH(OH)CH_2$—$NH(CH_2)_6NH_2$] are thereby obtained.

(2) 16 g (wet form) of the cross-linked aminohexyl-dextran obtained in paragraph (1) are treated in the same manner as described in Example 1-(2), whereby 20 g of a water-insoluble tannin preparation [i.e., chinese gallotannin bound by absorption to the cross-linked aminohexyl-dextran] are obtained.

(3) 2 g (wet form) of the water-insoluble tannin preparation obtained in paragraph (2) are treated in the same manner as described in paragraphs (3) and (4) of Example 1, whereby 2 g (wet form) of an immobilized aminoacylase preparation [i.e., water-insoluble tannin-aminoacylase preparation binding ferric ion thereto] are obtained. The immobilized aminoacylase preparation thus obtained shows an aminoacylase activity of 540$\mu$ moles/hr/2 g (wet form) of said preparation.

EXAMPLE 9

(1) 4 g of cellulose powder (manufactured by Toyo Roshi Co. under the trade name "Filter pulp No. 4") are added to 120 ml of an aqueous 25% sodium hydroxide solution, and the mixture is allowed to stand at 25° C. for 30 minutes. The wet cellulose is collected by filtration and washed with water. 20 g of the wet cellulose thus obtained are suspended in 150 ml of an aqueous 0.1 M sodium bicarbonate solution. The suspension is adjusted to a pH of 11.5, and 0.4 g of cyanogen bromide is added thereto. The mixture is then stirred at 20° to 25° C. for about 8 minutes. During the reaction, the pH is maintained at 11 to 11.5 by the use of an aqueous 5 N sodium hydroxide solution. After the reaction, the precipitates are collected by filtration and washed first with an aqueous 0.1 M sodium bicarbonate solution cooled to about 4° C. and then with cool water. The cyanogen bromide-activated cellulose thus obtained is suspended in 150 ml of an aqueous solution (pH 10) containing hexamethylenediamine (hexamethylenediamine content: 2.3 g/150 ml). The suspension is stirred at 25° C. for 2 hours. After the reaction, the precipitates are collected by filtration and washed first with an aqueous 0.1 M sodium bicarbonate solution and then with water. 15 g (wet form) of aminohexyl-cellulose [i.e., cellulose—O—$CONH(CH_2)_6NH_2$] are thereby obtained.

(2) 15 g (wet form) of the aminohexyl-cellulose obtained in paragraph (1) are treated in the same manner as described in Example 1-(2), whereby 20 g (wet form) of a water-insoluble tannin preparation [i.e., chinese gallotannin bound by adsorption to the aminohexyl-cellulose] are obtained.

(3) 2 g (wet form) of the water-insoluble tannin preparation obtained in paragraph (2) are treated in the same manner as described in paragraphs (3) and (4) of Example 1, whereby 2 g (wet form) of an immobilized aminoacylase preparation [i.e., water-insoluble tannin-aminoacylase preparation binding ferric ion thereto] are obtained. The immobilized aminoacylase preparation thus obtained shows an aminoacylase activity of 3,500$\mu$ moles/hr/2 g (wet form) of said preparation.

EXAMPLE 10

2 g (wet form) of the water-insoluble tannin-aminoacylase preparation obtained in the same manner as described in Example 1-(3) are suspended in 20 ml of 0.2 M acetylmethionine solution (pH 7.0) containing $5 \times 10^{-4}$ M of cobaltous ion. 5 ml of an aqueous solution (pH 7.0) containing 2% ferric chloride, 2% sodium acetate and 2% sodium tartrate are added gradually to the suspension while keeping the suspension at a pH of about 7.0 with sodium hydroxide. The precipitates are collected by filtration and washed with water. 2 g (wet form) of an immobilized aminoacylase preparation [i.e., water-insoluble tannin-aminoacylase preparation binding ferric ion thereto] are thereby obtained. The immobilized aminoacylase preparation thus obtained shows an aminoacylase activity of 4,000$\mu$ moles/hr/2 g (wet form) of said preparation.

EXAMPLE 11

2 g of the water-insoluble tannin-aminoacylase preparation obtained in the same manner as described in Example 1-(3) are treated in the same manner as described in Example 1-(4) except that a 1% ferrous sulfate solution is used instead of a 1% ferric chloride solution, whereby 2 g (wet form) of an immobilized aminoacylase preparation [i.e., water-insoluble tannin-aminoacylase preparation binding ferrous ion thereto] are obtained. The immobilized aminoacylase preparation thus obtained shows an aminoacylase activity of 3,000$\mu$ moles/hr/2 g (wet form) of said preparation.

EXAMPLE 12

(1) 32 g (wet form) of a water-insoluble tannin preparation obtained in the same manner as described in Example 1-(2) are suspended in 100 ml of an aqueous 1% potassium persulfate solution, and the suspension is allowed to stand at 25° C. for 20 hours. Then, the precipitates are collected by filtration and washed with water. 32 g (wet form) of a partially oxidized water-insoluble tannin preparation are thereby obtained.

(2) 2 g (wet form) of the partially oxidized water-insoluble tannin preparation obtained in paragraph (1) are treated in the same manner as described in paragraphs (3) and (4) of Example 1, whereby 2 g (wet form) of an immobilized aminoacylase preparation [i.e., water-insoluble tannin-aminoacylase preparation binding ferric ion thereto] are obtained. The immobilized aminoacylase preparation thus obtained shows an aminoacylase activity of 5,300$\mu$ moles/hr/2 g (wet form) of said preparation.

What we claim is:

1. A method for preparing an immobilized aminoacylase preparation which comprises the steps of:
   (i) contacting tannin with a water-insoluble, hydrophilic carrier selected from the group consisting of:
   Polysaccharide—O—CONH—A—H,
   Polysaccharide—O—$CH_2CH(OH)CH_2NH$—A—H,
   Polysaccharide—O—$CH_2CH(OH)CH_2O$—A—H, Polysaccharide—O—CH₂CH(OH)CH₂—B—CH₂CH(OH)CH₂NH—A—H,
Polysaccharide—O—CONH—A—NH₂,
Polysaccharide—O—CH₂CH(OH)CH₂NH—A—NH₂,
Polysaccharide—O—CH₂CH(OH)CH₂—B—CH₂CH(OH)CH₂NH—A—NH₂,
Polysaccharide—O—CONH—A—OH,
Polysaccharide—O—CH₂CH(OH)CH₂NH—A—OH,
Polysaccharide—O—CH₂CH(OH)CH₂O—A—OH,
Polysaccharide—O—CH₂CH(OH)CH₂—B—CH₂CH(OH)CH₂NH—A—OH,
Polysaccharide—O—CH₂CH(OH)CH₂—B—CH₂CH(OH)CH₂O—A—OH,
Polysaccharide—O—CONH—A—COOH,
Polysaccharide—O—CH₂CH(OH)CH₂NH—A—COOH,
Polysaccharide—O—CH₂CH(OH)CH₂—B—CH₂CH(OH)CH₂NH—A—COOH and

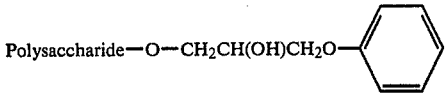

wherein A is alkylene having one to 16 carbon atoms which is optionally interrupted by a group selected from the class consisting of —O— and —NH—, B is a group of the formula: —(CH₂)$_n$— or —O(CH₂)$_n$O—, and n is an integer of 1 to 6, in an aqueous solvent to give a water-insoluble tannin preparation,
(ii) contacting aminoacylase with said water-insoluble tannin preparation in an aqueous solvent to give a water-insoluble tannin-aminoacylase preparation, and
(iii) contacting said water-insoluble tannin-aminoacylase preparation with ferric or ferrous ion in an aqueous solvent.

2. An immobilized aminoacylase preparation obtained by the method claimed in claim 1.

* * * * *